US011883956B2

(12) United States Patent
Hong et al.

(10) Patent No.: US 11,883,956 B2
(45) Date of Patent: Jan. 30, 2024

(54) WEARABLE GRAVITY COMPENSATION APPARATUS CAPABLE OF MULTIPLE DEGREES OF FREEDOM OF MOVEMENT

(71) Applicant: AGENCY FOR DEFENSE DEVELOPMENT, Daejeon (KR)

(72) Inventors: Man Bok Hong, Daejeon (KR); Gwang Tae Kim, Daejeon (KR); Yong Cheol Kim, Daejeon (KR); Jun Woo Kim, Daejeon (KR)

(73) Assignee: AGENCY FOR DEFENSE DEVELOPMENT

( * ) Notice: Subject to any disclaimer, the term of this patent is extended or adjusted under 35 U.S.C. 154(b) by 480 days.

(21) Appl. No.: 17/110,114

(22) Filed: Dec. 2, 2020

(65) Prior Publication Data
US 2021/0299854 A1 Sep. 30, 2021

(30) Foreign Application Priority Data

Mar. 27, 2020 (KR) .................. 10-2020-0037495
Oct. 22, 2020 (KR) .................. 10-2020-0137509

(51) Int. Cl.
*A61F 5/01* (2006.01)
*B25J 9/00* (2006.01)
*A61H 1/02* (2006.01)

(52) U.S. Cl.
CPC ............. *B25J 9/0006* (2013.01); *A61F 5/013* (2013.01); *A61H 1/0274* (2013.01); *A61H 2201/165* (2013.01); *A61H 2201/1671* (2013.01)

(58) Field of Classification Search
CPC ...... B25J 9/0006; A61F 5/013; A61H 1/0274; A61H 2201/165; A61H 2201/1671
See application file for complete search history.

(56) References Cited

U.S. PATENT DOCUMENTS

| 10,561,515 B2* | 2/2020 | Doyle .................. A61B 90/60 |
| 2013/0090580 A1* | 4/2013 | Hong .................. B25J 9/0072 |
| | | 601/33 |

(Continued)

FOREIGN PATENT DOCUMENTS

| JP | 2019-188598 | 10/2019 | ............. B25J 11/00 |
| KR | 10-1721518 | 3/2017 | ............. E04H 12/22 |

(Continued)

OTHER PUBLICATIONS

Korean Official Action issued in related Korean Patent Application Serial No. 10-2020-0037495, dated Jun. 17, 2021 (10 pages).

*Primary Examiner* — Jerrah Edwards
*Assistant Examiner* — Aren Patel
(74) *Attorney, Agent, or Firm* — HAYES SOLOWAY P.C.

(57) ABSTRACT

The wearable gravity compensation apparatus capable of multiple degrees of freedom of movement according to an example embodiment includes a main frame configured to be fixable to a back of a user, a base link rotatably connected to the main frame around a first rotation axis, a front extension link having one end rotatably connected to the base link around a second rotation axis intersecting the first rotation axis, the front extension link extending to a front of the base link, a rear extension link connected to the base link, the rear extension link extending to a rear of the base link, a guide positioned above the base link, the guide provided on the main frame, a slider configured to be slidable along the guide, a gravity compensation elastic member having one end fixed to the main frame, and the other end fixed to the slider.

13 Claims, 10 Drawing Sheets

(56) References Cited

U.S. PATENT DOCUMENTS

| | | | | |
|---|---|---|---|---|
| 2018/0177670 A1* | 6/2018 | Shim | ................ | B25J 9/0006 |
| 2018/0360636 A1* | 12/2018 | Rahman | ................ | A61F 5/013 |
| 2020/0163787 A1* | 5/2020 | Goldfarb | ................ | A61F 5/013 |
| 2020/0281796 A1* | 9/2020 | Lakany | ................ | A61H 1/0277 |

FOREIGN PATENT DOCUMENTS

| | | | | |
|---|---|---|---|---|
| KR | 10-1802433 | 11/2017 | ............ | A61H 1/02 |
| KR | 10-1894922 | 10/2018 | ............ | B65D 19/44 |
| KR | 10-2048931 | 1/2020 | ............ | A01D 46/24 |

\* cited by examiner

WEARABLE GRAVITY COMPENSATION APPARATUS CAPABLE OF MULTIPLE DEGREES OF FREEDOM OF MOVEMENT

STATEMENT OF GOVERNMENT INTEREST

This research was financially supported by the Institute of Civil Military Technology Cooperation funded by the Defense Acquisition Program Administration and Ministry of Trade, Industry and Energy of Korean Government under Grant No. 19-CM-GU-01.

CROSS-REFERENCE TO RELATED APPLICATION(S)

This application claims the benefit of Korean Patent Application No. 10-2020-0037495, filed on Mar. 27, 2020, and Korean Patent Application No. 10-2020-0137509 filed on Oct. 22, 2020, in the Korean Intellectual Property Office, the entire disclosures of which are incorporated herein by reference for all purposes.

BACKGROUND

1. Field of the Invention

Example embodiments relate to a wearable gravity compensation apparatus capable of multiple degrees of freedom of movement.

2. Description of the Related Art

A gravity compensation apparatus refers to an apparatus that generally includes a combination of a plurality of links and an elastic member such as a spring, and compensates for a weight of a load provided at an end of the apparatus. The gravity compensation apparatus, which is an apparatus designed to support the weight of the load provided at the end of the apparatus without an actuator even when the load provided at the end of the apparatus is placed in any position within an operating radius, is being used as a desk lamp, a camera weight compensation apparatus, and the like. The gravity compensation apparatus may support the weight of the load at any position in a non-powered manner without an actuator. Thus, the gravity compensation apparatus has an advantage in that it has a simple system configuration, and is highly reliable and inexpensive in comparison to a power-type apparatus including multiple actuators and links such as a robot arm.

Due to such advantages of the gravity compensation apparatus, a gravity compensation apparatus technology has recently been applied as a form of an upper limb exoskeleton apparatus that is worn by a person so as to be able to assist in an upper limb operation of dealing with a heavy object. That is, a conventional gravity compensation apparatus has been developed in the form of an upper limb exoskeleton robot using an actuator, a controller, and the like so as to assist in the upper limb operation of industrial workers. However, due to disadvantages such as a heavy and complicated system resulting from the use of a battery and an actuator, high cost, and the like, there was a limitation in its practical application.

The upper limb exoskeleton apparatus may be especially useful for a soldier that performs mine detection. The soldier that performs mine detection carries a mine detector weighing about 4 kg to perform mine detection tasks. Especially, in Korea, a situation where the soldier that performs mine detection has to work mainly on a slope such as a mountain occurs frequently. In this case, the weight of the mine detector during a mine detection operation increases the fatigue of the soldier's arm, and thus acts as a factor that interferes with the mine detection operation requiring high concentration. Accordingly, there is a need for a technology for a wearable gravity compensation apparatus capable of multiple degrees of freedom of movement, which may support the weight of the mine detector and accommodate various movements of a user.

The above description has been possessed or acquired by the inventor(s) in the course of conceiving the present disclosure and is not necessarily an art publicly known before the present application is filed.

SUMMARY

An aspect provides a wearable gravity compensation apparatus capable of multiple degrees of freedom of movement for implementing a non-powered upper limb exoskeleton apparatus, thereby enabling gravity compensation within a predetermined operating radius range.

According to an aspect, there is provided a wearable gravity compensation apparatus capable of multiple degrees of freedom of movement including a main frame configured to be fixable to a back of a user, a base link rotatably connected to the main frame around a first rotation axis, a front extension link having one end rotatably connected to the base link around a second rotation axis intersecting the first rotation axis, the front extension link extending to a front of the base link, a rear extension link connected to the base link, the rear extension link extending to a rear of the base link, a guide positioned above the base link, the guide provided on the main frame, a slider configured to be slidable along the guide, a gravity compensation elastic member having one end fixed to the main frame, and the other end fixed to the slider, a first coupling link rotatably connected to the slider, a link plate rotatably connected to each of the main frame and the first coupling link, and a second coupling link rotatably connected to each of the link plate and the rear extension link.

The wearable gravity compensation apparatus capable of multiple degrees of freedom of movement may include a coupling link rotatably connected to each of the rear extension link and the slider.

The rear extension link may be fixed to the base link to move integrally with the base link.

The front extension link may be configured to be capable of two degrees of freedom of movement with respect to the main frame.

The wearable gravity compensation apparatus capable of multiple degrees of freedom of movement may further include a support part connected to the other end of the front extension link, the support part configured to be capable of supporting an arm of the user, and to be capable of two degrees of freedom of movement with respect to the front extension link.

The support part may include a support base rotatably connected to the front extension link around a third rotation axis, a support plate provided on an upper side of the support base, the support plate configured to be capable of two degrees of freedom of movement with respect to the support base, and a support joint configured to connect the support base and the support plate to each other.

The support joint may be a universal joint or a ball joint.

The third rotation axis may be parallel to the second rotation axis.

The wearable gravity compensation apparatus capable of multiple degrees of freedom of movement may further include an arm support band connected to the support part, the arm support band configured to surround the arm of the user.

The front extension link may be formed in a plurality, and a plurality of front extension links may include a first front extension link having one end rotatably connected to the base link, and a second front extension link having one end rotatably connected to the other end of the first front extension link.

A rotation axis of the second front extension link relative to the first front extension link may be parallel to the second rotation axis.

The wearable gravity compensation apparatus capable of multiple degrees of freedom of movement may further include a connection elastic member having one end connected to the first front extension link, and the other end connected to the second front extension link.

The plurality of front extension links may further include a third front extension link having one end rotatably connected to the other end of the second front extension link, and the second front extension link may have one end connected to a lower side of the first front extension link, and the other end connected to a lower side of the third front extension link.

While the front extension link and the rear extension link rotate around the first rotation axis, the slider may be configured to slide along the guide, and the elastic member may be deformed.

The wearable gravity compensation apparatus capable of multiple degrees of freedom of movement may further include a body support band connected to the main frame, the body support band configured to surround a body of the user.

According to another aspect, there is provided a wearable gravity compensation apparatus capable of multiple degrees of freedom of movement including a main frame, a base link rotatably connected to the main frame around a first rotation axis, a front extension link having one end rotatably connected to the base link around a second rotation axis intersecting the first rotation axis, the front extension link extending to a front of the base link, a rear extension link connected to the base link, the rear extension link extending to a rear of the base link, a guide positioned above the base link, the guide provided on the main frame, a slider configured to be slidable along the guide, a gravity compensation elastic member having one end fixed to the main frame, and the other end fixed to the slider, a coupling link rotatably connected to each of the rear extension link and the slider, and a support part connected to the other end of the front extension link, the support part configured to be capable of supporting an arm of a user, and to be capable of two degrees of freedom of movement with respect to the front extension link.

The support part may include a support base rotatably connected to the front extension link around a third rotation axis, a support plate provided on an upper side of the support base, the support plate configured to be capable of two degrees of freedom of movement with respect to the support base, and a support joint configured to connect the support base and the support plate to each other.

According to still another aspect, there is provided a wearable gravity compensation apparatus capable of multiple degrees of freedom of movement including a main frame, a base link rotatably connected to the main frame around a first rotation axis, a front extension link having one end rotatably connected to the base link around a second rotation axis intersecting the first rotation axis, the front extension link extending to a front of the base link, a rear extension link connected to the base link, the rear extension link extending to a rear of the base link, a guide positioned above the base link, the guide provided on the main frame, a slider configured to be slidable along the guide, a gravity compensation elastic member having one end fixed to the main frame, and the other end fixed to the slider, and a coupling link rotatably connected to each of the rear extension link and the slider. The front extension link may be formed in a plurality, and a plurality of front extension links may include a first front extension link having one end rotatably connected to the base link, and a second front extension link having one end rotatably connected to the other end of the first front extension link.

Additional aspects of example embodiments will be set forth in part in the description which follows and, in part, will be apparent from the description, or may be learned by practice of the disclosure.

A wearable gravity compensation apparatus capable of multiple degrees of freedom of movement according to an example embodiment may compensate for a weight of a load while providing free movement by accommodating multiple degrees of freedom of movement of a wearer.

In addition, the wearable gravity compensation apparatus capable of multiple degrees of freedom of movement according to an example embodiment may have an elastic member for gravity compensation on a back of a user without having an additional elastic member in the vicinity of an arm of the user so that the apparatus is provided in a compact size in the vicinity of a portion that may interfere with a body of the user, for example, the arm of the user, thereby minimizing interference with the body of the user.

In addition, the wearable gravity compensation apparatus capable of multiple degrees of freedom of movement according to an example embodiment may have a support part provided in the form of a ball joint on a portion that supports the arm of the user, thereby further increasing the degree of freedom, and improving the user's feeling of wearing.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
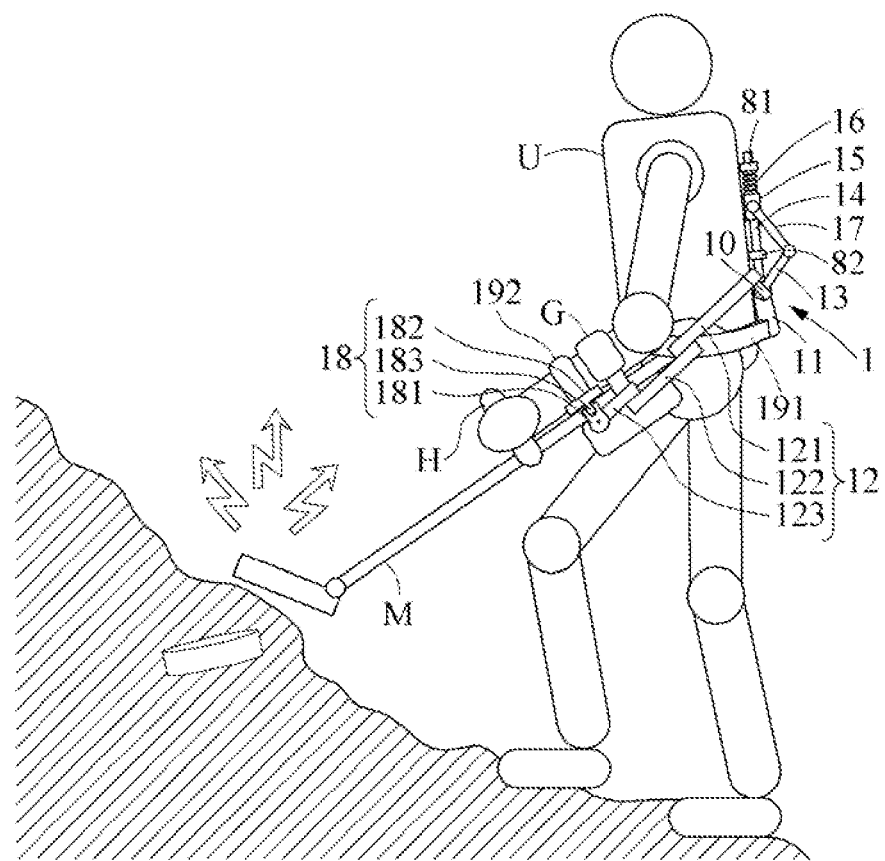
FIGS. 1 and 2 are schematic diagrams illustrating a user wearing a wearable gravity compensation apparatus capable of multiple degrees of freedom of movement according to an example embodiment, and a mine detector is omitted in FIG. 2.

Hereinafter, example embodiments will be described in detail with reference to the accompanying drawings. The scope of the right, however, should not be construed as limited to the example embodiments set forth herein. Various modifications may be made to the example embodiments. Here, examples are not construed as limited to the example embodiments and should be understood to include all changes, equivalents, and replacements within the idea and the technical scope of the example embodiments.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood. that the terms "comprises," "comprising," "includes," and/or "including," when used herein, specify the presence of stated features, integers, operations, elements, and/or components, but do not preclude the presence or addition of one or more other features, integers, operations, elements, components, and/or groups thereof.

Unless otherwise defined, all terms, including technical and scientific terms, used herein have the same meaning as commonly understood by those skilled in the art to which the example embodiments pertain. Terms, such as those defined in commonly used dictionaries, are to be interpreted as having a meaning that is consistent with their meaning in the context of the relevant art, and are not to be interpreted in an idealized or overly formal sense unless expressly so defined herein.

Regarding the reference numerals assigned to the components in the drawings, it should be noted that the same components will be designated by the same reference numerals, wherever possible, even though they are shown in different drawings. Also, in the description of example embodiments, detailed description of well-known related structures or functions will be omitted when it is deemed that such description will cause ambiguous interpretation of the example embodiments.

In addition, terms such as first, second, A, B, (a), (b), and the like may be used herein to describe components of the example embodiments. These terms are only used to distinguish one component from another component, and essential, order, or sequence of corresponding components are not limited by these terms. It will be understood that when one component is referred to as being "connected to", "coupled to", or "linked to" another component, one component may be "connected to", "coupled to", or "linked to" another component via a further component although one component may be directly connected to or directly linked to another component.

The same name may be used to describe a component included in an example embodiment and a component having a common function in another example embodiment. Unless otherwise mentioned, the description on the example embodiment may be applicable to the other example embodiment and thus, duplicated description will be omitted for conciseness.

Figure 2:
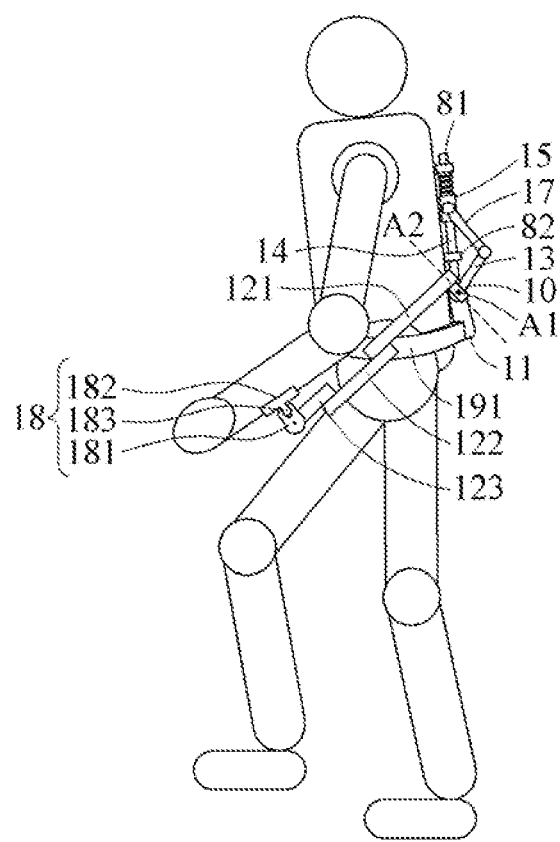
Figure 3:
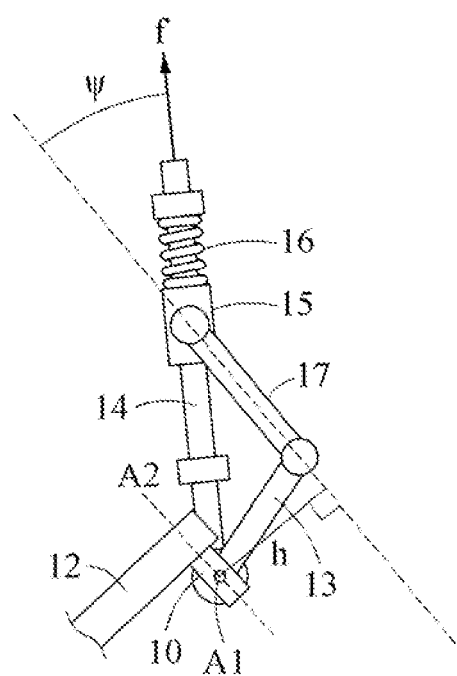
FIG. 3 is an enlarged schematic diagram of a portion that performs gravity compensation in a wearable gravity compensation capable of multiple degrees of freedom of movement according to an example embodiment.

FIGS. 1 and 2 are schematic diagrams illustrating a user wearing a wearable gravity compensation apparatus capable of multiple degrees of freedom of movement according to an example embodiment. In FIG. 2, a mine detector is omitted. FIG. 3 is an enlarged schematic diagram of a portion that performs gravity compensation in a wearable gravity compensation capable of multiple degrees of freedom of movement according to an example embodiment. A mine detector M may include a handle H gripped by a user by hand, and a forearm fixing band G that may be fixed to a forearm of the user.

Referring to FIGS. 1 to 3, a wearable gravity compensation apparatus capable of multiple degrees of freedom of movement according to an example embodiment 1 (hereinafter referred to as "gravity compensation apparatus") may operate in a non-powered form that does not additionally receive power from the outside. The gravity compensation apparatus 1 may largely include a support part which is a distal end connected to an arm of a user U or a load, a front extension link which is an motion implementation unit for implementing movement of the arm, and a slider and an elastic member which are a gravity compensation unit for supporting a weight of a load transmitted through the motion implementation unit. The support part and the front extension link of the gravity compensation apparatus 1 may have a compact structure while implementing multiple degrees of freedom of movement of the user.

The gravity compensation apparatus 1 may allow the front extension link which is the motion implementation unit that implements multiple degrees of freedom of movement, and the slider and the elastic member which are the gravity compensation unit to be in a non-flexible state, thereby configuring the motion implementation unit that moves closely with an arm of a wearer to be simpler and slimmer. The gravity compensation apparatus 1 may minimize interference during operation between the arm of the wearer or a heavy object to be operated and the gravity compensation apparatus. The gravity compensation apparatus 1 may arrange the elastic member for gravity compensation on a back of the user where movement of the user's arm does not reach, thereby implementing multiple degrees of freedom of movement of the wearer's arm while minimizing interference, and providing a gravity compensation function.

The gravity compensation apparatus 1 may include a main frame 11, a base link 10, a front extension link 12, a rear extension link 13, a guide 14, a slider 15, a gravity compensation elastic member 16, a coupling link 17, a support part 18, a body support band 191, an arm support band 192, and a shoulder support band 193.

The main frame 11 may be fixable to the user's back. A longitudinal direction of the main frame 11 may be parallel to a longitudinal direction of the user's back. In the drawings, a vertical direction may denote the longitudinal direction of the main frame 11. The main frame 11 may be fixed to the user's back through the body support band 191 connected to the main frame 11.

The base link 10 may be rotatably connected to the main frame 11 around a first rotation axis A1. The base link 10 may be capable of one degree of freedom of movement with respect to the main frame 11. The base link 10 may support a front extension link 12 and a rear extension link 13 to be described later. The front extension link 12 may extend to a front of the base link 10, and the rear extension link 13 may extend to a rear of the base link 10. The base link 10 and the front extension link 12 may be movable relative to each other, and the base link 10 and the rear extension link 13 may be limited in movement relative to each other.

The front extension link 12 may have one end rotatably connected to the base link 10. The front extension link 12 may be rotatably connected to the base link 10 around a second rotation axis A2 intersecting the first rotation axis A1. The front extension link 12 may be capable of two degrees of freedom of movement with respect to the main frame 11. The front extension link 12 may move in a manner in which a plurality of segments rotate with each other as the user moves his/her arm to the left or right, and the front extension link 12 may rotate around the base link 10 as the user moves his/her arm upward or downward.

It should be noted that the front extension link 12 may be directly rotatably connected to the base link 10, or may be rotatably connected to the base link 10 through a connection member although not illustrated. The front extension link 12 may be formed in plurality.

A plurality of front extension links 12 may include a first front extension link 121, a second front extension link 122, and a third front extension link 123. It should be noted that the number of the plurality of front extension links 12 may be two or at least four. Hereinafter, it will be described based on a configuration in which the number of the plurality of front extension links 12 are three.

The first front extension link 121, the second front extension link 122, and the third front extension link 123 may be provided in parallel in a direction toward the front from the base link 10. The first front extension link 121 may have one end rotatably connected to the base link 10, and the other end rotatably connected to the second front extension link 122. The second front extension link 122 may have one end rotatably connected to the first front extension link 121, and the other end rotatably connected to the third front extension link 123. The third front extension link 123 may have one end rotatably connected to the second front extension link 122, and the other end configured to rotatably support the support part 18.

A rotation axis of the second front extension link 122 relative to the first front extension link 121 may be parallel to the second rotation axis A2. In other words, a rotation axis that rotatably connects the first front extension link 121 and the second front extension link 122 to each other may be parallel to the second rotation axis A2 described above. In the same manner, a rotation axis that rotatably connects the second front extension link 122 and the third front extension link 123 to each other may be parallel to the second rotation axis A2. According to the above-described structure, both the second rotation axis A2 and the rotation axis that connects two adjacent front extension links among the plurality of front extension links 12 to each other may be provided in parallel, and accordingly the user may freely move his/her arm to the left or right.

In addition, as the front extension link 12 is provided in plurality, the user may independently move multiple joints of his/her arm. For example, the user may move his/her arm to the left or right around his/her shoulder joint in a state in which his/her elbow joint is fixed. In this case, while the first front extension link 121 and the second front extension link 122, and the second front extension link 122 and the third front extension link 123 do not move relative to each other, only the first front extension link 121 may be driven in a manner of rotating around the base link 10. As another example, when the user intends to use only his/her elbow joint in a state in which his/her shoulder joint is fixed, only relative movement between the first front extension link 121 and the second front extension link 122 may be implemented.

The rear extension link 13 may be connected to the base link 10, and may extend to the rear of the base link 10. The rear extension link 13 may be integrally fixed so as to limit movement relative to the base link 10. The rear extension link 13 may be fixed to the base link 10 to move integrally with the base link 10, and accordingly the rear extension link 13, the coupling link 17, and the slider 15 may implement one degree of freedom of movement. Unnecessary movements may be limited except for movements for gravity compensation, thereby improving durability of the apparatus.

The guide 14 may be positioned above the base link 10, and may be provided on the main frame 11. A longitudinal direction of the guide 14 may be arranged along the longitudinal direction of the main frame 11. The guide 14 may be part of the main frame 11. The main frame 11 may include movement limiting members 81 and 82 for setting an area of the guide 14. The first movement limiting member 81 may be provided at an upper end of the guide 14, and the second movement limiting member 82 may be provided at a lower end of the guide 14.

The slider 15 may be slidable along the guide 14. The slider 15 may be slidable between the first movement limiting member 81 and the second movement limiting member 82.

The gravity compensation elastic member 16 may have one end fixed to the main frame 11, and the other end fixed to the slider 15. For example, the gravity compensation elastic member 16 may have one end connected to the first movement limiting member 81, and the other end connected to an upper surface of the slider 15. The gravity compensation elastic member 16 may apply a force for gravity compensation.

The coupling link 17 may have one end rotatably connected to the rear extension link 13, and the other end rotatably connected to the slider 15. The coupling link 17 may transmit, to the slider 15, power by which the rear extension link 13 rotates around the first rotation axis A1. For example, when the rear extension link 13 rotates in a counterclockwise direction based on the drawings, the slider 15 may slide upward along the guide 14.

The support part 18 may be provided at an end of the front extension link 12 that is furthest away from the base link 10. The support part 18 may support the user's arm. The support part 18 may be capable of two degrees of freedom of movement with respect to the front extension link 12. The support part 18 may include a support base 181 rotatably connected to the front extension link 12, a support plate 182 provided on an upper side of the support base 181, and configured to be capable of two degrees of freedom of movement with respect to the support base 181, and a support joint 183 configured to connect the support base 181 and the support plate 182 to each other. The support joint 183 may be a universal joint or a ball joint. The support joint 183 may assist the support plate 182 to move with two degrees of freedom with respect to the support base 181.

A rotation axis (a third rotation axis A3) around which the support base 181 is rotatably connected to the front extension link 12 may be parallel to the second rotation axis A2. According to the above-described structure, it may be possible to reduce interference of the gravity compensation apparatus 1 with the user's arm in a motion in which the user lowers and raises his/her arm around his/her shoulder joint. In addition, since the support plate 182 is connected to the support base 181 through the support joint 183, the support plate 182 may be rotatable around an axis parallel to an axis around which the two adjacent front extension links among the plurality of front extension links 12 are connected to each other. According to the above-described structure, it may be possible to reduce the interference of the gravity compensation apparatus 1 with the user's arm in a motion in which the user moves his/her arm to the left or right.

The arm support band 192 may fix the support part 18 to the user's arm. The arm support band 192 may be connected to the support part 18, and may surround the user's arm. The shoulder support band 193 may fix the main frame 11 to a shoulder of the user. The shoulder support band 192 may surround the user's shoulder.

The gravity compensation apparatus 1 may allow the base link 10, the front extension link 12, and the support part 18 that implement multiple degrees of freedom of movement to be in a non-flexible state, thereby implementing the motion implementation unit that moves closely with the user's arm. Regarding the implementation of such a motion, the base link 10, the front extension link 12, and the support part 18 may not be provided with an elastic member for gravity compensation, and thus a simpler and slimmer design may be possible. Thus, interference between the user's arm or load and the gravity compensation apparatus may be minimized. The elastic member for gravity compensation may be arranged on the user's back, thereby minimizing overall interference with multiple degrees of freedom of movement of the user's arm.

The gravity compensation apparatus may include a connection elastic member 71 that is fixed to the two adjacent front extension links among the plurality of front extension links to provide a buffer force. For example, the connection elastic member 71 may include a first connection elastic member 711 having one end connected to the first front extension link 121, and the other end connected to the second front extension link 122, and a second connection elastic member 712 having one end connected to the second front extension link 122, and the other end connected to the third front extension link 123. The connection elastic member 71 may assist the front extension link 12 so as to maintain a default position in a situation where no external force is applied. It should be noted that the connection elastic member 71 is not an elastic member for gravity compensation. The gravity compensation apparatus according to an example embodiment is characterized in that a portion provided in the vicinity of the user's arm is provided in a compact size by arranging the elastic member for gravity compensation on the user's back.

Hereinafter, a gravity compensation mechanism of the gravity compensation apparatus 1 will be described in detail with reference to FIG. 3. When the front extension link 12 of the gravity compensation apparatus 1 rotates in accordance with the movement of the user's arm, the base link 10 connected to the front extension link 12 may rotate around the first rotation axis A1. Hereinafter, for ease of description, it will be described on the basis of rotation of the base link 10 in a counterclockwise direction. When the base link 10 rotates in a counterclockwise direction around the first rotation axis A1, the coupling link 13 may rotate in a clockwise direction of the base link 10. The coupling link 13 may slide the slider 15 upward while rotating in a clockwise direction. As the slider 15 slides upward, the gravity compensation elastic member 16 may be compressed. The compressed gravity compensation elastic member 16 may transmit a gravity compensation force to the front extension link 12 through a restoring force. On the basis of such a principle, the gravity compensation elastic member 16 may provide a support moment to the front extension link 12 and the support part 18.

A load with a weight applied to the user's arm, such as a mine detector, may generate a torque to rotate the base link 10 through the user's arm. When the torque is denoted as τ 12, and a force applied to the gravity compensation elastic member 16 through the slider 15 in response to input of the torque is denoted as f, the following relational expression may be obtained.

$$\tau_{12} = \left(\frac{h}{\cos\psi}\right)f = \left(\frac{h}{\cos\psi}\right)K(l - l_0)$$

Referring to FIG. 3, h may denote a vertical distance from a center of the base link 10 to the coupling link 17, and ψ may denote an angle between a virtual extension line of the coupling link 17 and the guide 14. K may denote rigidity of the gravity compensation elastic member 16, $l_0$ may denote an initial length of the gravity compensation elastic member 16 before the gravity compensation elastic member 16 is displaced, and l may denote a current length of the gravity compensation elastic member 16. On the basis of the above expression, the gravity compensation apparatus 1 having a gravity compensation value for a predetermined torque inputted in an operation area may be designed.

Figure 4:
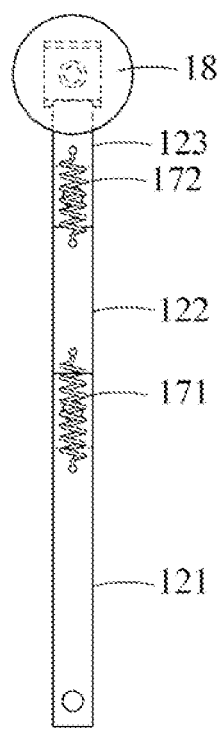
FIGS. 4 to 6 are schematic diagrams illustrating shapes of a plurality of links and a support part that are deformed in accordance with movement of a user according to an example embodiment.
Figure 5:
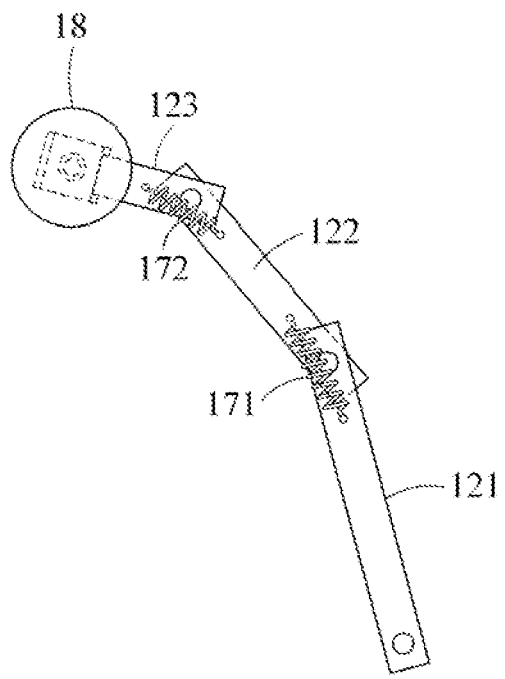
Figure 6:
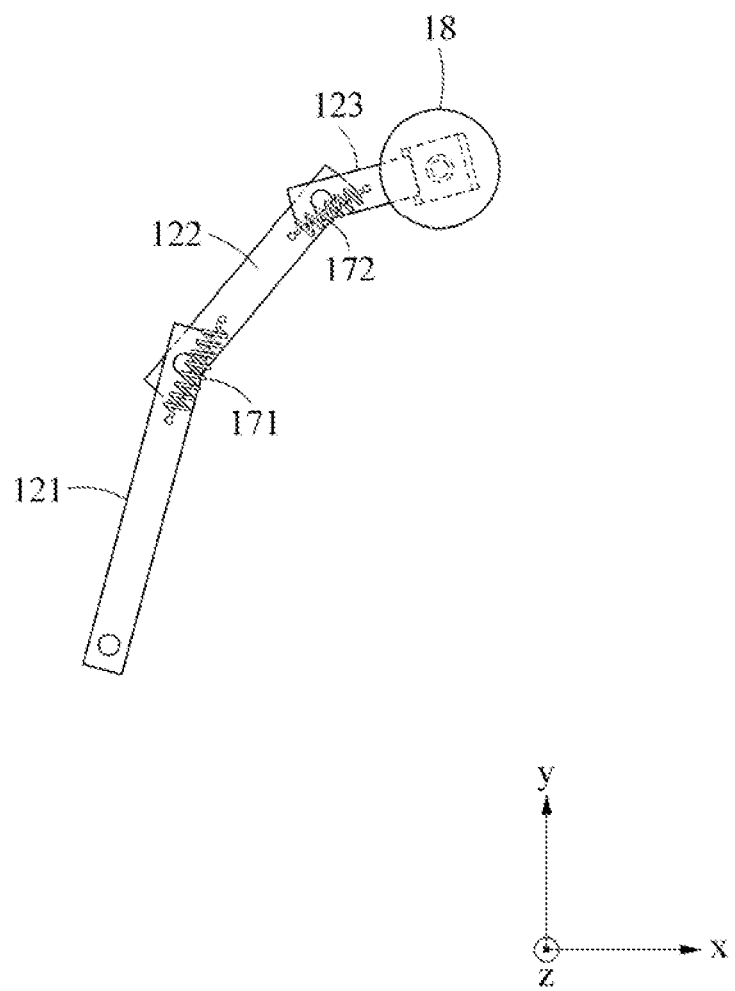

FIGS. 4 to 6 are schematic diagrams illustrating shapes of a plurality of links and a support part that are deformed in accordance with movement of a user according to an example embodiment.

Referring to FIGS. 4 to 6, the user may freely move his/her arm to the left or right in a state of wearing the gravity compensation apparatus. For example, in a state in which the user extends his/her arm to the front (+y direction), the front extension link 12 may extend in a direction parallel to the user's arm. When the user moves his/her arm to the left (+x direction) or to the right (−x direction), the plurality of front extension links 12 may be deformed in accordance with the movement of the user's arm. Specifically, the first front extension link 121 may rotate around the second rotation axis A2, the second front extension link 122 may rotate around a rotation axis parallel to the second rotation axis A2 with respect to the first front extension link 121, and the third front extension link 123 may rotate around a rotational axis parallel to the second rotational axis A2 with respect to the second front extension link 122.

Figure 7:
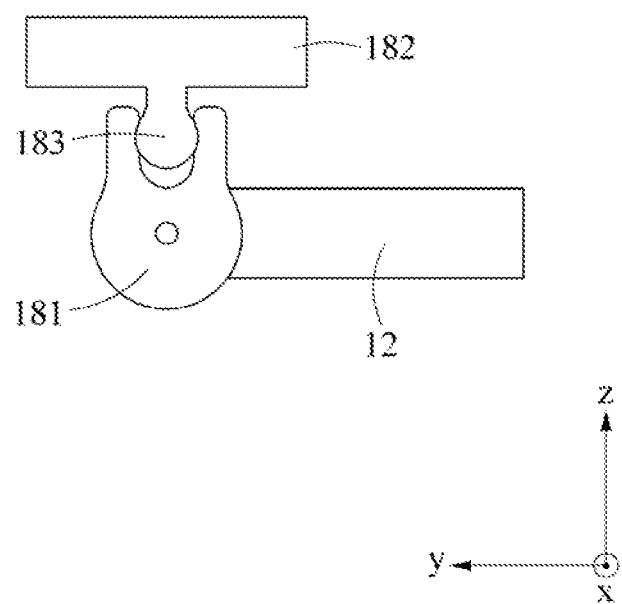
FIGS. 7 and 8 are enlarged schematic diagrams illustrating a support part of a wearable gravity compensation apparatus capable of multiple degrees of freedom of movement according to an example embodiment.
Figure 8:
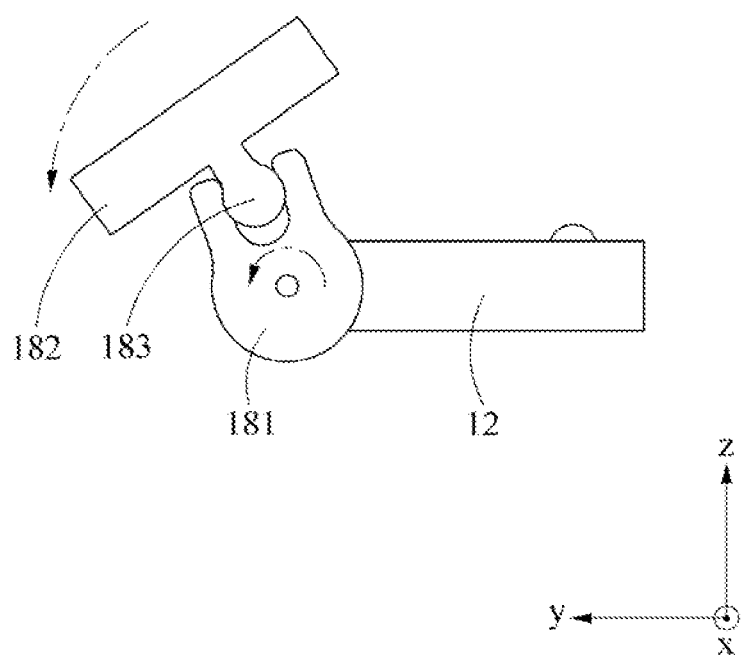

FIGS. 7 and 8 are enlarged schematic diagrams illustrating a support part of a wearable gravity compensation apparatus capable of multiple degrees of freedom of movement according to an example embodiment.

Referring to FIGS. 7 and 8, the support part 18 may provide a degree of freedom of the movement of the user. For example, the support base 181 of the support part 18 may be rotatably connected to the front extension link 12, and the support plate 182 may be connected to the support base 181 through the support joint 183 so as to be capable of two degrees of freedom of movement. According to the above-described structure, the user may perform relatively free movement without interference with the gravity compensation apparatus.

Figure 9:
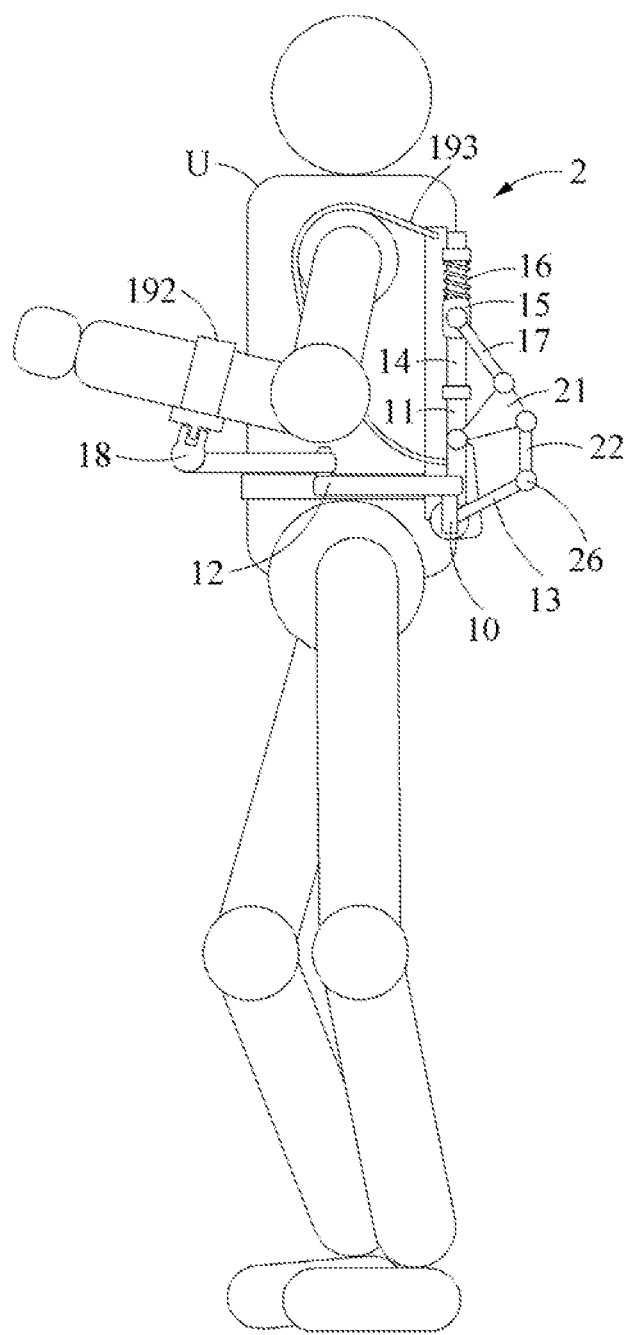
FIG. 9 is a schematic diagram illustrating a user wearing a wearable gravity compensation apparatus capable of multiple degrees of freedom of movement according to an example embodiment.
Figure 10:
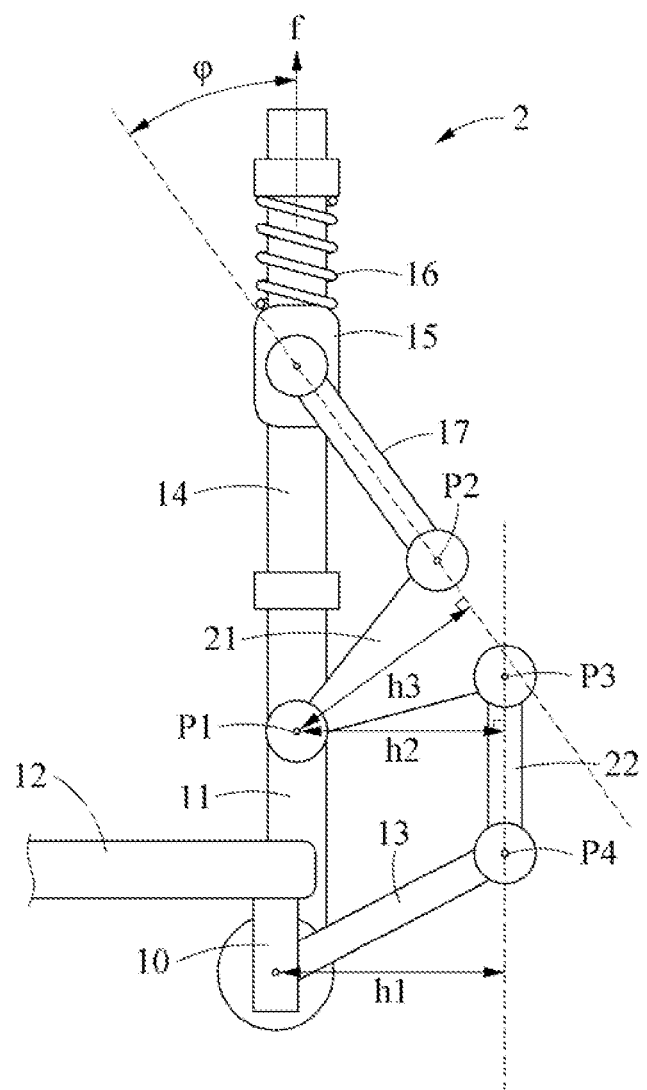
FIG. 10 is an enlarged schematic diagram of a portion that performs gravity compensation in a wearable gravity compensation capable of multiple degrees of freedom of movement according to an example embodiment.

FIG. 9 is a schematic diagram illustrating a user wearing a wearable gravity compensation apparatus capable of multiple degrees of freedom of movement according to an example embodiment, and FIG. 10 is an enlarged schematic diagram of a portion that performs gravity compensation in a wearable gravity compensation capable of multiple degrees of freedom of movement according to an example embodiment.

Referring to FIGS. 9 and 10, a gravity compensation apparatus 2 may include a main frame 11, a base link 10, a front extension link 12, a rear extension link 13, a guide 14, a slider 15, a gravity compensation elastic member 16, a first coupling link 17, a link plate 21, a second coupling link 22, a support part 18, a body support band 191, an arm support band 192, and a shoulder support band 193.

The first coupling link 17 may be rotatably connected to the slider 15. The link plate 21 may be rotatably connected to each of the main frame 11 and the first coupling link 17. The second coupling link 22 may be rotatably connected to each of the link plate 21 and the rear extension link 13.

A load applied to the user's arm may apply a force to the base link 10 through the front extension link 12 by way of the user's arm. As a result, the load may generate a load torque to rotate the base link 10 with respect to the main frame 11. The load torque may move the slider 15 and compress the gravity compensation elastic member 16. The compressed gravity compensation elastic member 16 may apply a resistance torque for the load torque to the base link 10. When the resistance torque is denoted as $\tau_{Spring}$, the following relational expression may be obtained.

$$\tau_{Spring} = -K\left(\frac{h_1 \cdot h_3}{h_2 \cdot \cos\psi}\right)(l_0 - l)$$

Here, h1 may denote a vertical distance from a rotation center of the base link 10 relative to the main frame 11 to a virtual line that connects two rotation joints P3 and P4 to each other, h2 may denote a vertical distance from a rotation center P1 of the link plate 21 relative to the main frame 11 to a virtual line that connects two rotation joints P2 and P3 to each other, and h3 may denote a vertical distance from the rotation center P1 of the link plate 21 relative to the main frame 11 to a virtual line that connects two rotation joints provided opposite ends of the first coupling link 17 to each other.

Through the link plate 21 and the second coupling link 22, the gravity compensation apparatus 2 may have a larger number of links and joints, and thus may have a large number of design parameters. The large number of design parameters may help design the apparatus so as to better compensate for the load torque.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A wearable gravity compensation apparatus capable of multiple degrees of freedom of movement comprising:
   a main frame configured to be fixable to a back of a user;
   a base link rotatably connected to the main frame around a first rotation axis;
   a front extension link having one end rotatably connected to the base link around a second rotation axis intersecting the first rotation axis, the front extension link extending to a front of the base link;
   a rear extension link connected to the base link, the rear extension link extending to a rear of the base link;
   a guide positioned above the base link, the guide provided on the main frame;
   a slider configured to be slidable along the guide;
   a gravity compensation elastic member having one end fixed to the main frame, and the other end fixed to the slider;
   a coupling link rotatably connected to each of the rear extension link and the slider; and
   a support part connected to the other end of the front extension link, the support part configured to be capable of supporting an arm of the user, and to be capable of two degrees of freedom of movement with respect to the front extension link, wherein the support part comprises:
   a support base rotatably connected to the front extension link around a third rotation axis;
   a support plate provided on an upper side of the support base, the support plate configured to be capable of two degrees of freedom of movement with respect to the support base; and
   a support joint configured to connect the support base and the support plate to each other, and permit free lateral movement to the left or to the right of a supported arm.

2. The wearable gravity compensation apparatus capable of multiple degrees of freedom of movement of claim 1, wherein the rear extension link is fixed to the base link to move integrally with the base link.

3. The wearable gravity compensation apparatus capable of multiple degrees of freedom of movement of claim 2, wherein the front extension link is configured to be capable of two degrees of freedom of movement with respect to the main frame.

4. The wearable gravity compensation apparatus capable of multiple degrees of freedom of movement of claim 1, wherein the support joint is a universal joint or a ball joint.

5. The wearable gravity compensation apparatus capable of multiple degrees of freedom of movement of claim 1, wherein the third rotation axis is parallel to the second rotation axis.

6. The wearable gravity compensation apparatus capable of multiple degrees of freedom of movement of claim 1, further comprising:
   an arm support band connected to the support part, the arm support band configured to surround the arm of the user.

7. The wearable gravity compensation apparatus capable of multiple degrees of freedom of movement of claim 1, wherein
   the front extension link is formed in a plurality, and
   a plurality of front extension links comprises:
   a first front extension link having one end rotatably connected to the base link; and
   a second front extension link having one end rotatably connected to the other end of the first front extension link.

8. The wearable gravity compensation apparatus capable of multiple degrees of freedom of movement of claim 7, wherein a rotation axis of the second front extension link relative to the first front extension link is parallel to the second rotation axis.

9. The wearable gravity compensation apparatus capable of multiple degrees of freedom of movement of claim 7, further comprising:

a connection elastic member having one end connected to the first front extension link, and the other end connected to the second front extension link.

10. The wearable gravity compensation apparatus capable of multiple degrees of freedom of movement of claim 7, wherein
the plurality of front extension links further comprises a third front extension link having one end rotatably connected to the other end of the second front extension link, and
the second front extension link has one end connected to a lower side of the first front extension link, and the other end connected to a lower side of the third front extension link.

11. The wearable gravity compensation apparatus capable of multiple degrees of freedom of movement of claim 1, wherein, while the front extension link and the rear extension link rotate around the first rotation axis, the slider is configured to slide along the guide, and the elastic member is deformed.

12. The wearable gravity compensation apparatus capable of multiple degrees of freedom of movement of claim 1, further comprising:
a body support band connected to the main frame, the body support band configured to surround a body of the user.

13. A wearable gravity compensation apparatus capable of multiple degrees of freedom of movement comprising:
a main frame configured to be fixable to a back of a user;
a base link rotatably connected to the main frame around a first rotation axis;
a front extension link having one end rotatably connected to the base link around a second rotation axis intersecting the first rotation axis, the front extension link extending to a front of the base link;
a rear extension link connected to the base link, the rear extension link extending to a rear of the base link;
a guide positioned above the base link, the guide provided on the main frame;
a slider configured to be slidable along the guide;
a gravity compensation elastic member having one end fixed to the main frame, and the other end fixed to the slider;
a first coupling link rotatably connected to the slider;
a link plate rotatably connected to each of the main frame and the first coupling link;
a second coupling link rotatably connected to each of the link plate and the rear extension link; and
a support part connected to the other end of the front extension link, the support part configured to be capable of supporting an arm of the user, and to be capable of two degrees of freedom of movement with respect to the front extension link, wherein the support part comprises:
a support base rotatably connected to the front extension link around a third rotation axis;
a support plate provided on an upper side of the support base, the support plate configured to be capable of two degrees of freedom of movement with respect to the support base; and
a support joint configured to connect the support base and the support plate to each other, and permit free lateral movement to the left or to the right of a supported arm.

* * * * *